United States Patent
Becker

(10) Patent No.: US 7,660,389 B1
(45) Date of Patent: Feb. 9, 2010

(54) SAMPLE ALIGNMENT MECHANISM FOR X-RAY DIFFRACTION INSTRUMENTATION

(75) Inventor: Bruce L. Becker, Madison, WI (US)

(73) Assignee: Bruker AXS, Inc., Madison, WI (US)

( * ) Notice: Subject to any disclaimer, the term of this patent is extended or adjusted under 35 U.S.C. 154(b) by 61 days.

(21) Appl. No.: 12/191,622

(22) Filed: Aug. 14, 2008

Related U.S. Application Data

(60) Provisional application No. 60/956,535, filed on Aug. 17, 2007.

(51) Int. Cl.
*G01N 23/20* (2006.01)
*H05G 1/02* (2006.01)

(52) U.S. Cl. .................... 378/81; 378/205; 378/208

(58) Field of Classification Search ............ 378/81, 378/205, 208
See application file for complete search history.

(56) References Cited

U.S. PATENT DOCUMENTS

| | | | | |
|---|---|---|---|---|
| 3,614,229 A | * | 10/1971 | Denne ................ | 356/31 |
| 3,723,006 A | * | 3/1973 | Thomas, Jr. ............ | 356/30 |
| 3,736,426 A | * | 5/1973 | Anderson et al. ........ | 378/73 |
| 4,759,130 A | * | 7/1988 | Goldowsky .............. | 33/1 N |
| 4,770,593 A | * | 9/1988 | Anderson .............. | 414/222.08 |
| 6,608,883 B2 | * | 8/2003 | Olson et al. ............ | 378/79 |
| 6,888,920 B2 | * | 5/2005 | Blank et al. ........... | 378/81 |
| 7,274,769 B2 | * | 9/2007 | Nordmeyer et al. ....... | 378/80 |

OTHER PUBLICATIONS

Cipriani, et al., "Automation of Sample Mounting for Macromolecular Crystallography", Biologoical Crystallography, Acta Crystallographica, Section D, 2006, pp. 1251-1259, 2006 International Union of Crystallography, Denmark.
http://www.mitegen.com/products/micromounts/why.shtml, "Why Use MicroMounts?".

* cited by examiner

*Primary Examiner*—Allen C. Ho
*Assistant Examiner*—Thomas R Artman
(74) *Attorney, Agent, or Firm*—Law Offices of Paul E. Kudirka

(57) ABSTRACT

In an X-ray diffraction apparatus, a sample holder has a sample mounted on a pin extending a known distance from a cap that mates with a magnetized base on a goniometer. The sample is mechanically positioned in the center of an X-ray beam by a first movable arm which is located in a precise position relative to the goniometer base by a positioning mechanism and a mechanism that forces the pin into engagement with the first arm. The sample has a known height on the pin with respect to the cap and therefore, the sample can repeatedly be located in the center of the X-ray beam without the use of complex centering arrangements. In order to allow the sample holder to be removed from the goniometer base, a linkage is provided that releases the pin from the first arm.

20 Claims, 4 Drawing Sheets

SAMPLE ALIGNMENT MECHANISM FOR X-RAY DIFFRACTION INSTRUMENTATION

BACKGROUND

This invention relates to X-ray diffraction systems. X-ray diffraction is a non-destructive technique for the qualitative and quantitative analysis of crystalline material samples, which are generally provided in the form of crystals or powders. In accordance with this technique, an X-ray beam is generated by an X-ray tube with a stationary anode, by a conventional rotating anode X-ray source or by a synchrotron source and directed toward the material sample under investigation. When the X-rays strike the sample, they are diffracted according to the atomic structure of the sample.

A typical laboratory system 100 for performing single crystal diffraction experiments normally consists of five components as shown in FIG. 1. The components include an X-ray source 102 that produces a primary X-ray beam 104 with the required radiation energy, focal spot size and intensity. X-ray optics 106 are provided to condition the primary X-ray beam 104 to a conditioned, or incident, beam 108 with the required wavelength, beam focus size, beam profile and divergence. A goniometer 110 is used to establish and manipulate geometric relationships between the incident X-ray beam 108, the crystal sample 112 and the X-ray detector 114. The incident X-ray beam 108 strikes the crystal sample 112 and produces scattered X-rays 116 which are recorded in the detector 114. A sample alignment and monitor assembly comprises a sample illuminator 118, typically a laser, that illuminates the sample 112 and a sample monitor 120, typically a video camera, which generates a video image of the sample to assist users in positioning the sample in the instrument center and monitoring the sample state and position.

The goniometer 110 allows the crystal sample 112 to be rotated around several axes. Precise crystallography requires that the sample crystal 112 be aligned to the center of the goniometer 110 and maintained in that center when rotated around the goniometer rotational axes during data collection. The 112 goniometer typically has a magnetizable mounting base with an extension on which a sample holder can be mounted.

One type of magnetic-style sample holder 200 that is commonly used with conventional goniometers is shown in FIG. 2. This sample holder consists of a Spine cap 202 with a collar 204 that fits over the goniometer mounting base extension (not shown in FIG. 2) and is magnetically held on the goniometer. A pin 210 with a central axis extends from the Spine cap 202. The collar 204 has a precise inside diameter 206 that mates with the outer surface of the goniometer mounting base extension to radially position the sample holder with respect to the central axis. A mounting face 208 seats against a corresponding face on the goniometer mounting base to axially position the cap 202. A conventional Spine sample holder is described in more detail in "Automation of Sample Mounting for Macromolecular Crystallography", Cipriani et al., *Acta Crystallographica*, D62, pp. 1251-1259 (2006) which is hereby incorporated by reference in its entirety.

A crystal mounting arrangement 212 is affixed to the free end of the pin 210. The crystal mounting arrangement has a small sample well (not shown in FIG. 2) in which the crystal is placed for measurement. The crystal mounting arrangement 212 may, for example, be a Micromount™ crystal mount developed and sold by MiTeGen LLC, P.O. Box 3867, Ithaca, N.Y. 14852.

Traditionally, once a sample in placed in such a sample holder and the sample holder has been mounted on the goniometer mounting base, the sample is not expected to be aligned in the X-ray beam path. Consequently, the goniometer mounting base must be adjusted to position the sample in the center the X-ray beam. Traditional X-ray diffraction instrumentation has required either manual adjustment of a crystal sample position in the beam path, or more recently, automated positioning based on the use of an imaging system, such as illuminator 118 and imaging system 120, microscope, control software, and at least three linear actuators. These arrangements are complicated and expensive.

SUMMARY

In accordance with the principles of the invention, a sample holder with a pin having a known distance between the crystal mounting arrangement and the Spine cap mounting surface is mechanically positioned in the center of an X-ray beam by a first movable arm which is located in a precise position relative to the goniometer base by a positioning mechanism and a mechanism that forces the pin into engagement with the first arm. Since the crystal mounting arrangement has a known height on the pin with respect to the Spine cap mounting surface and therefore with respect to the magnetic goniometer base, the sample can repeatedly be located in the center of the X-ray beam without the use of complex centering arrangements. In order to allow the sample holder to be removed from the goniometer base, a linkage is provided that releases the pin from the first arm.

In one embodiment, the pin is forced into engagement with the first arm by a second movable arm that opposes the first movable arm and a spring that urges the first and second arms toward each other so that the pin is grasped between the first and second arms.

In another embodiment, the linkage that releases the pin from the first arm comprises a linkage connected between the first and second arms that move the first arm away from the pin when the second arm is moved away from the pin.

In still another embodiment, the first arm has a V-block on one end that engages the pin and the second arm has an anvil that forces the pin into engagement with the V-block when the arms are urged towards each other.

In yet another embodiment, the first arm has a pair of V-blocks on one end that engages the pin and the second arm has an anvil that contacts the pin between the V-blocks and forces the pin into engagement with the V-blocks.

In a further embodiment, the positioning mechanism comprises a first V-block attached to the goniometer base and a second V-block that is attached to the first arm and that mates with the first V-block.

DETAILED DESCRIPTION

In accordance with the principles of the invention, the crystal mounting arrangement 212 is fixed on the pin 210 so that the sample well is located at a precise distance from the mounting face 208 of the Spine cap 202. Typically, the distance of the sample well from the mounting face 208 does not vary more than approximately 20 microns from sample holder to sample holder. Because the height of the sample is dictated by the distance of the sample well to the base of the sample holder, the positioning mechanism needs only to position the central axis of the sample pin. This is done by trapping the pin between an anvil and a set of V-blocks. The shaft of the sample pin is assumed to be straight (tests have indicated that the sample pins are straight enough for use with the inventive sample centering apparatus) and the diameter of the sample pin is also assumed to be substantially uniform (also shown to be true in tests). The magnetic goniometer base is machined so that it is smaller in diameter than the inside diameter of the Spine cap. This difference in dimensions allows the base of the sample holder to "float" on the magnetic goniometer base. Therefore, when the sample pin is forced into the V-blocks by the anvil, the central axis of the sample pin is precisely positioned. Although this arrangement produces a highly repeatable sample positioning, the focused x-ray beam that is applied to the sample must be large enough to compensate for variations in the repeatability of sample positioning.

Figure 1:
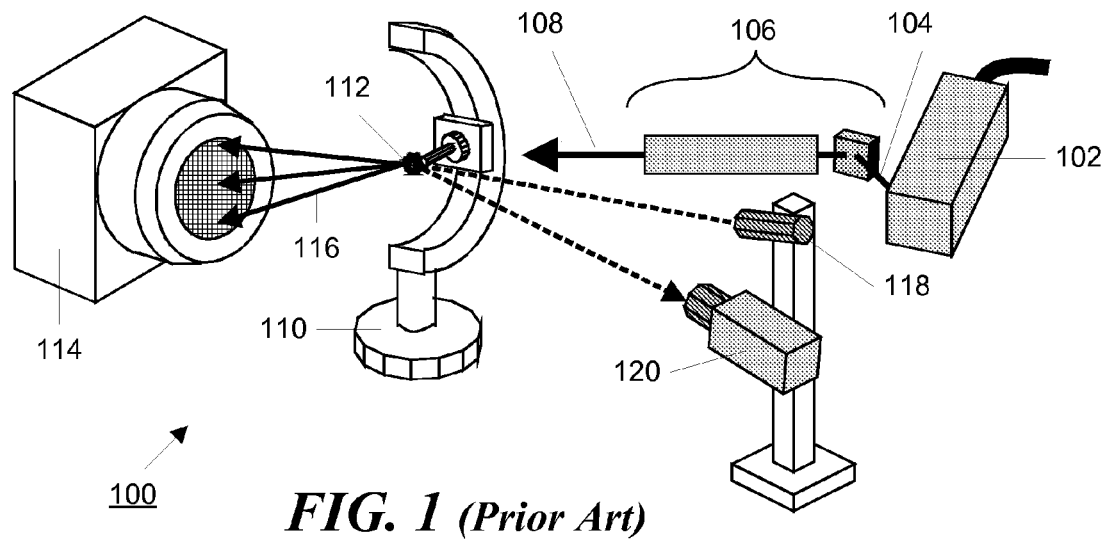
FIG. 1 is a schematic diagram of a conventional laboratory X-ray diffraction apparatus.
Figure 2:
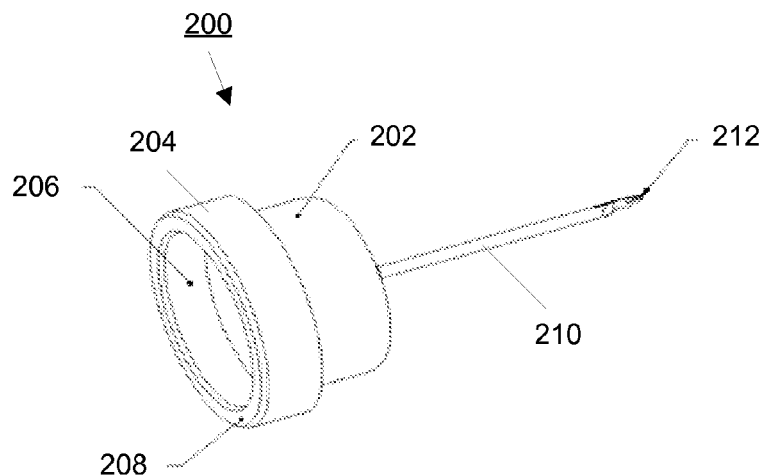
FIG. 2 is a perspective view of a conventional Spine cap showing the crystal mount.
Figure 3:
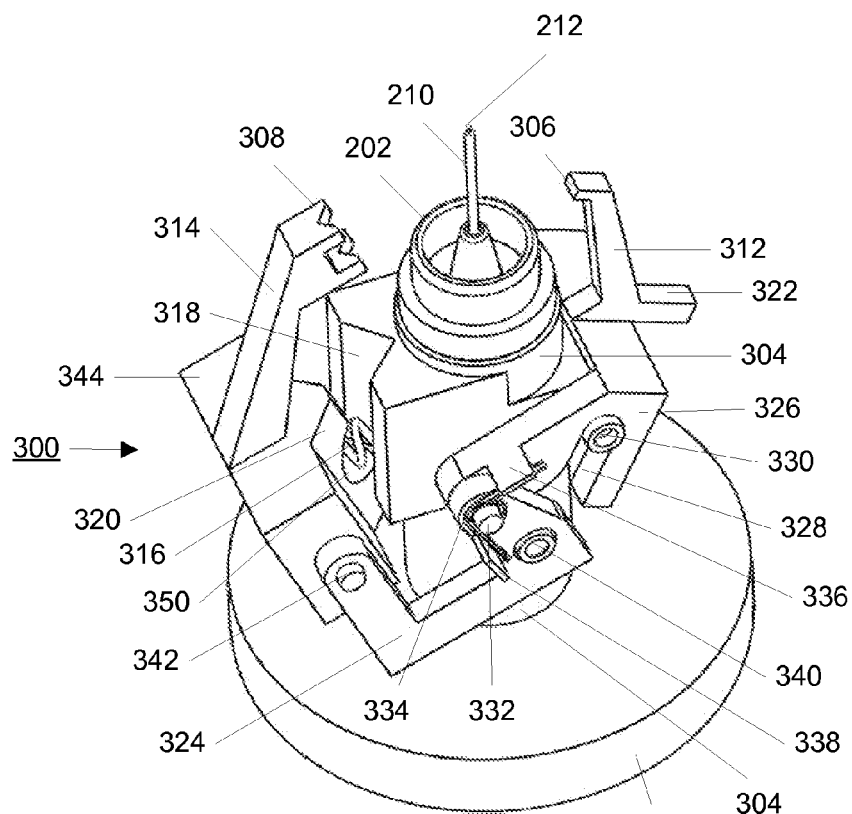
FIG. 3 is a perspective view of the inventive sample centering arrangement mounted on a conventional goniometer.

An illustrative embodiment 300 of the sample centering apparatus is shown in FIGS. 3-7. In these figures, the same parts have been given the same reference numerals to aid in identification. FIG. 3 is a perspective view of the centering apparatus mounted on a goniometer with a base 302 and a pedestal 304 which together comprise the goniometer phi stage so that the sample mounting arrangement rotates with the phi axis. As mentioned above, the Spine cap 202 sits on the magnetized top of pedestal 304 and positions the sample pin 210 and the crystal mounting 212 relative to the top of the goniometer pedestal 304.

An anvil 306 and pin V-blocks 308 and 310 are mounted on the ends of opposing arms 312 and 314, respectively, which pivot at their lower ends. The arms 312 and 314 are forced towards each other by a spring 316 (shown in more detail in FIG. 5) in order to position the pin 210. The arms 312 and 314 are pivoted because it is necessary to open and shut the pin V-blocks 308 and 310 and anvil 306 so that the sample holder 202 can be placed on and removed from the magnetic goniometer base 304. A positioner V-block 318 on the goniometer pedestal 304 mates with a V-block 320 on the arm 314 to precisely locate the arm 314 holding the pin V-blocks 308 and 310 when the anvil arm 312 and V-block arm 314 move toward each other.

When the sample holder 202 is to be loaded or unloaded, the phi axis of the goniometer 304 is oriented under a motorized actuator (not shown in FIG. 3) which pushes down on an extension 322 attached to the anvil arm 312. As described more fully below, a linkage 324 then causes the anvil arm 312 and pin V-block arm 314 to separate as shown in FIG. 3. When the actuator is lifted, the force of spring 316 closes the pin V-block arm 314. The linkage 324 together with a spring mechanism, in turn, closes the anvil arm 312 to position the sample pin 210.

Figure 4:
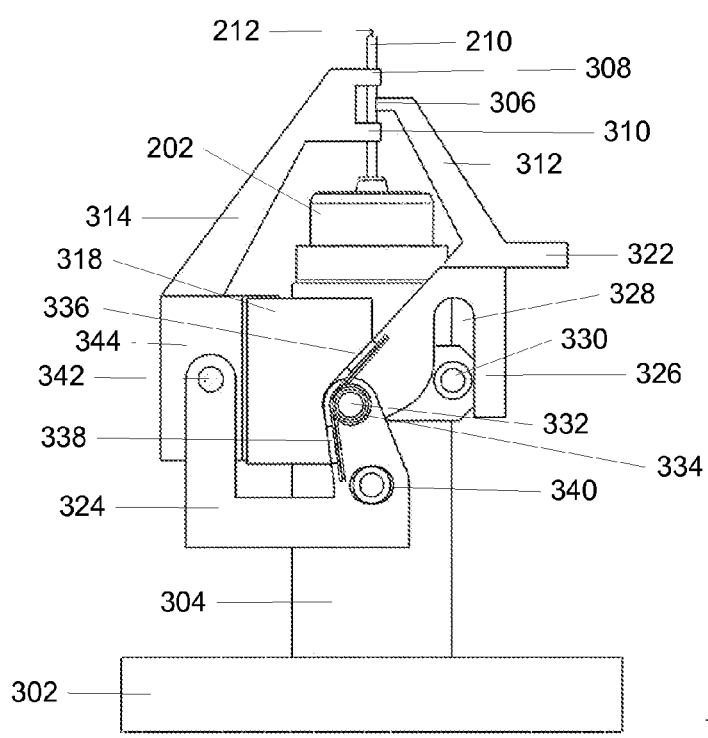
FIG. 4 is a side view of the sample centering arrangement shown in FIG. 3.

The linkage that separates the arms is shown in FIG. 3 and in FIG. 4, which is a side view of the mechanism that illustrates the arms 312 and 314 in their "closed" position. In particular, anvil arm 312 is mounted on a carrier 326 having slot 328 that slides over a pin 330, which is attached to pedestal 304 of the goniometer. The carrier 326 is attached to linkage 324 by pivot pin 332. A coil spring 334 surrounds the pivot pin 332 and bears against tabs 336 and 338 to maintain the carrier 326 and anvil arm 312 in the closed position.

Linkage 324 rotates around pivot pin 340 which is attached to goniometer pedestal 304. The other end of linkage 324 is attached by pivot pin 342 to carrier 344 on which V-block arm 314 and positioner V-block 320 are mounted.

Figure 5:
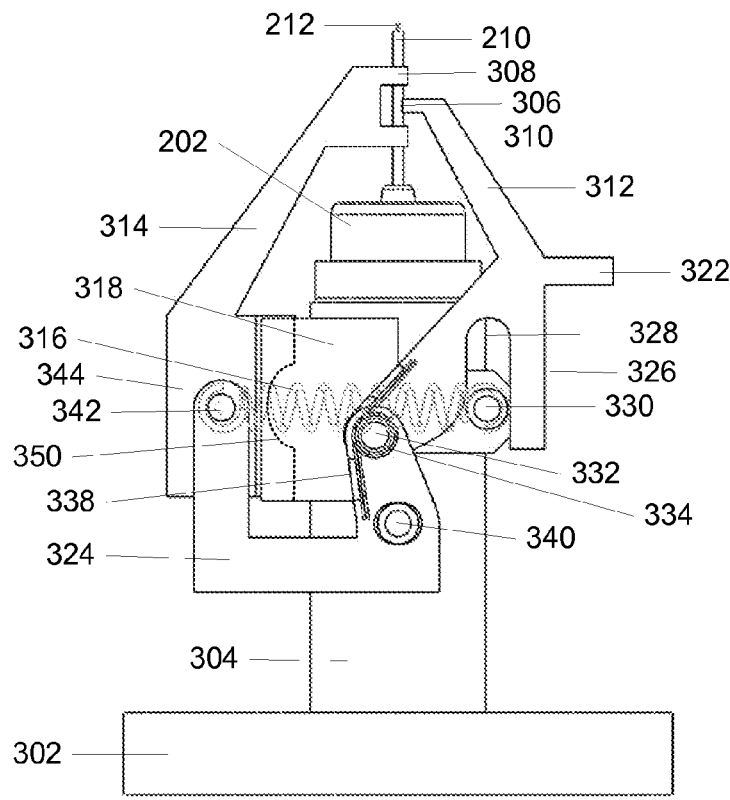
FIG. 5 is a side view of the sample centering arrangement illustrating an internal centering spring shown in phantom.

FIG. 5 shows a side view of the sample positioning mechanism which illustrates the spring 316 in more detail. The coil spring 316 is shown in phantom in FIG. 5 and extends between pin 330 and pin 342 passing through a hole in pedestal 304. The contraction of spring 316 firmly mates positioner V-blocks 318 and 320 to accurately position V-block arm 314 relative to the goniometer pedestal 304. A cutout 350 in the positioner V-block 320 allows the positioner V-block 320 to clear the spring 316 when the V-block arm 314 opens and closes.

Figure 6:
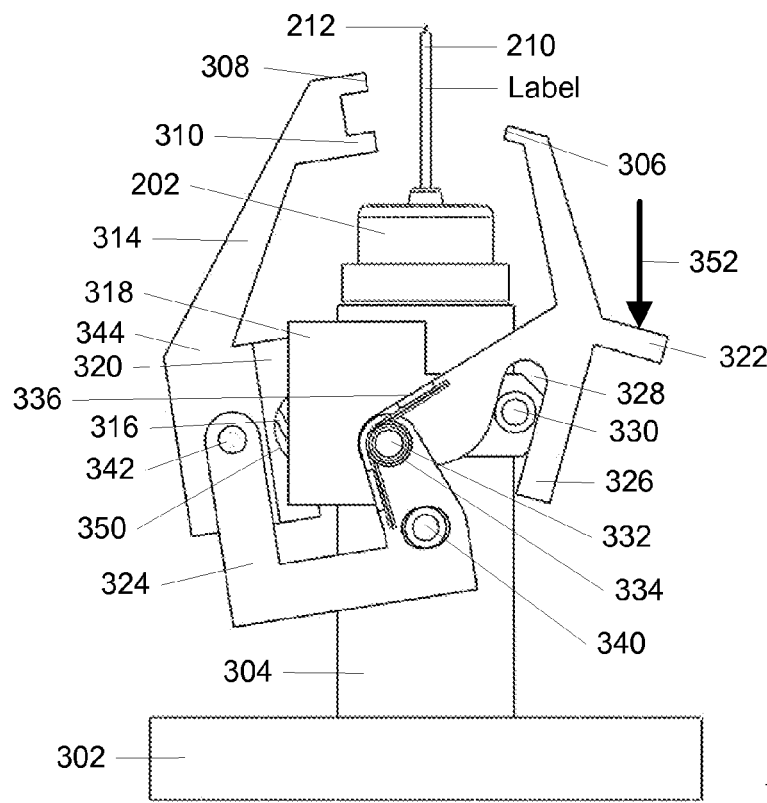
FIG. 6 is a side view of the sample centering arrangement illustrating the position of the centering arms when the mechanism begins to open to allow replacement of the Spine cap and sample.
Figure 7:
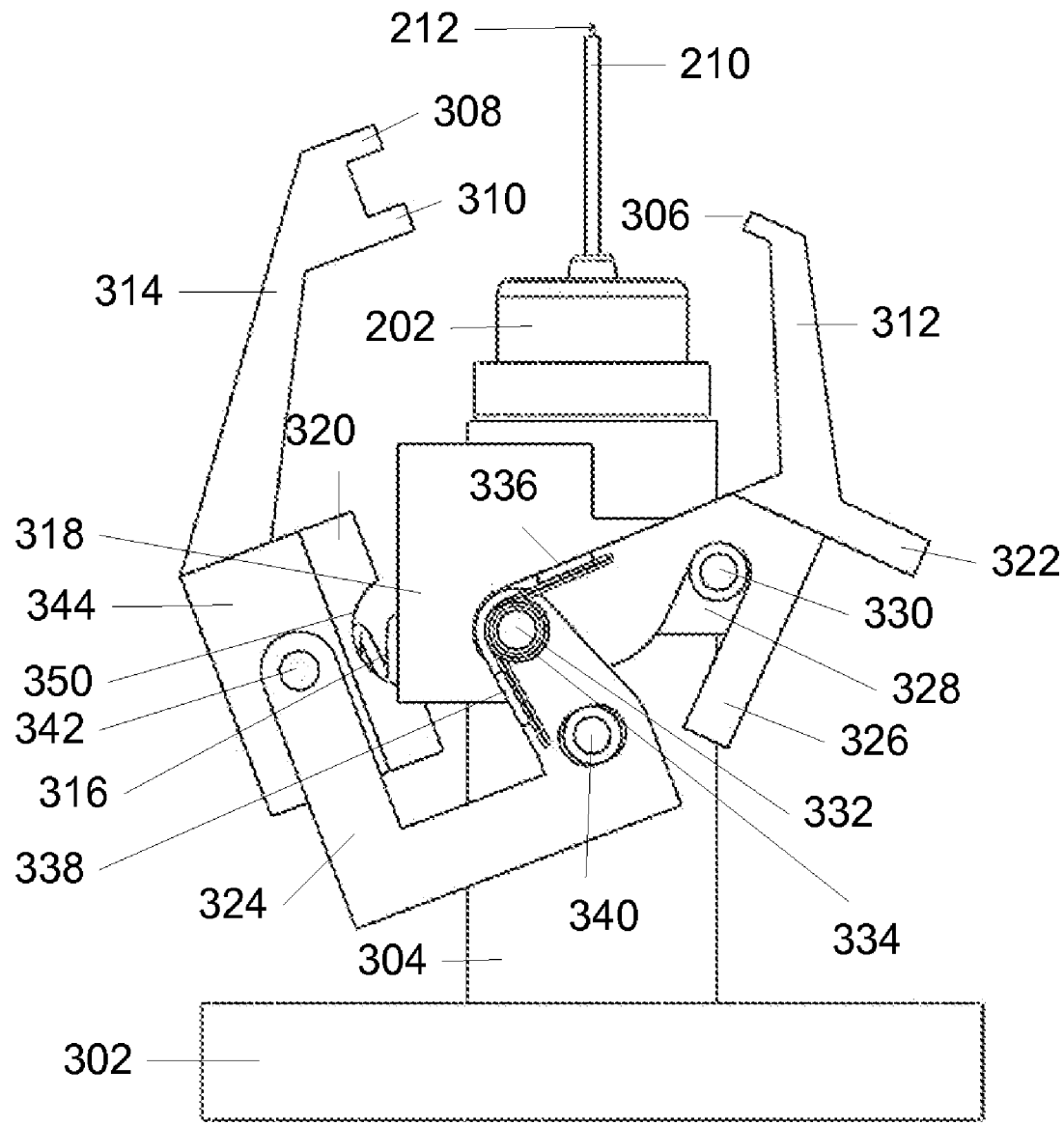
FIG. 7 is a side view of the sample centering arrangement illustrating the position of the centering arms when the mechanism is fully open.

FIGS. 6 and 7 illustrate the functioning of the arm and linkage mechanism as the sample positioning mechanism begins to open. As shown in FIG. 6, the mechanism is opened by a mechanical actuator (not shown in FIG. 6) that applies a downward force illustrated schematically by arrow 352 to the extension 322 of anvil arm 312. This force causes the slot 328 of carrier 326 to slide downwards over pin 330 and the carrier 326 to simultaneously rock backward, thereby moving the anvil arm 312 back from the sample pin 210. The rocking motion is transmitted to linkage 324 via pivot pin 332, flexing spring 334 in the process. Linkage 324, in turn, rotates around pivot pin 340 in the counterclockwise direction. This latter rotation applies a force outward and downward to carrier 344 via pivot pin 342. This latter force causes the carrier 344 to rock backward and away from the V-block 318, in turn, causing the V-block arm 314 to move away from the sample pin 210.

FIG. 7 shows the sample positioning mechanism in its fully opened position. In this position, carrier 326 has moved downward so that the pin 330 bears against the top of slot 328. Linkage 324 has rotated fully, pulling carrier 344 away from the goniometer pedestal 304 and extending spring 316 to its maximum extent. Arms 312 and 314 have opened to their maximum extent to allow the sample holder 202 to be removed from the goniometer base.

Although an illustrative embodiment is shown, different sample holders can be used as long as the sample is roughly held on the center axis of the pin, the sample distance from the magnetic goniometer base is uniform from sample holder to sample holder, and a magnetic base is used. In addition, it would be possible to use the anvil and V-block positioning arms to radially position the sample along the sample rod axis and then control the distance between the crystal mounting arrangement and the sample holder base using a conventional motorized axis and a visualization system.

While the invention has been shown and described with reference to a number of embodiments thereof, it will be recognized by those skilled in the art that various changes in form and detail may be made herein without departing from the spirit and scope of the invention as defined by the appended claims.

What is claimed is:

1. A sample alignment mechanism for X-ray diffraction instrumentation having a goniometer with a magnetized base and a sample holder having a pin that holds a sample and extends a known distance from a cap that mates with the magnetized base, the mechanism comprising:
- a first movable arm;
- a positioning mechanism that locates the first arm in a precise position relative to the goniometer base;
- a mechanism that forces the pin into engagement with the first arm; and
- a linkage that releases the pin from the first arm so that the sample holder can be removed from the goniometer base.

2. The sample alignment mechanism of claim 1 wherein the mechanism that forces the pin into engagement with the first arm comprises a second movable arm that opposes the first movable arm and a spring that urges the first and second arms toward each other so that the pin is grasped between the first and second arms.

3. The sample alignment mechanism of claim 2 wherein the linkage that releases the pin from the first arm comprises a linkage connected between the first and second arms that move the first arm away from the pin when the second arm is moved away from the pin.

4. The sample alignment mechanism of claim 2 wherein the first arm has a V-block on one end that engages the pin and the second arm has an anvil that forces the pin into engagement with the V-block when the arms are urged towards each other.

5. The sample alignment mechanism of claim 4 wherein the first arm has a pair of V-blocks on one end that engages the pin and the second arm has an anvil that contacts the pin between the V-blocks and forces the pin into engagement with the V-blocks.

6. The sample alignment mechanism of claim 1 wherein the positioning mechanism comprises a first V-block attached to the goniometer base and a second V-block that is attached to the first arm and that mates with the first V-block.

7. A goniometer for X-ray diffraction instrumentation for use with a sample holder having a pin that holds a sample and extends a known distance from a cap, the goniometer comprising:
- a magnetized base that extends into the cap;
- a first movable arm having a first end that pivots on the base and a second end that engages the pin;
- a positioning mechanism that locates the first arm in a precise position relative to the goniometer base;
- a second movable arm having a first end that pivots on the base and a second end that opposes the second end of the first movable arm;
- a mechanism that that urges the first and second arms toward each other so that the pin is grasped between the first and second arms; and
- a linkage that moves the first arm away from the second arm so that the sample holder can be removed from the goniometer base.

8. The goniometer of claim 7 wherein the mechanism that that urges the first and second arms toward each other comprises a spring.

9. The goniometer of claim 8 wherein the linkage that linkage that moves the first arm away from the second arm a linkage connected between the first and second arms that moves the first arm away from the pin when the second arm is moved away from the pin.

10. The goniometer of claim 7 wherein the first arm has a V-block on one end that engages the pin and the second arm has an anvil that forces the pin into engagement with the V-block when the arms are urged towards each other.

11. The goniometer of claim 10 wherein the first arm has a pair of V-blocks on one end that engages the pin and the second arm has an anvil that contacts the pin between the V-blocks and forces the pin into engagement with the V-blocks.

12. The goniometer of claim 7 wherein the positioning mechanism comprises a first V-block attached to the goniometer base and a second V-block that is attached to the first arm and that mates with the first V-block.

13. The goniometer of claim 7 wherein the first and second arms are mounted on the phi stage of the goniometer base.

14. X-ray diffraction apparatus, comprising:
- a sample holder having a pin that holds a sample and extends a known distance from a cap;
- a goniometer having a magnetized base that extends into the cap, a first movable arm having a first end that pivots on the base and a second end that engages the pin, a positioning mechanism that locates the first arm in a precise position relative to the goniometer base, a second movable arm having a first end that pivots on the base and a second end that opposes the second end of the first movable arm, a mechanism that that urges the first and second arms toward each other so that the pin is grasped between the first and second arms and a linkage that moves the first arm away from the second arm so that the sample holder can be removed from the goniometer base;
- an X-ray source; and
- an X-ray detector.

15. The X-ray diffraction apparatus of claim 14 wherein the mechanism that that urges the first and second arms toward each other comprises a spring.

16. The X-ray diffraction apparatus of claim 15 wherein the linkage that linkage that moves the first arm away from the second arm a linkage connected between the first and second arms that moves the first arm away from the pin when the second arm is moved away from the pin.

17. The X-ray diffraction apparatus of claim 16 wherein the first arm has a V-block on one end that engages the pin and the second arm has an anvil that forces the pin into engagement with the V-block when the arms are urged towards each other.

18. The X-ray diffraction apparatus of claim 17 wherein the first arm has a pair of V-blocks on one end that engages the pin and the second arm has an anvil that contacts the pin between the V-blocks and forces the pin into engagement with the V-blocks.

19. The X-ray diffraction apparatus of claim 14 wherein the positioning mechanism comprises a first V-block attached to the goniometer base and a second V-block that is attached to the first arm and that mates with the first V-block.

20. The X-ray diffraction apparatus of claim 14 wherein the first and second arms are mounted on the phi stage of the goniometer base.

* * * * *